US008481974B1

(12) United States Patent
Davis et al.

(10) Patent No.: US 8,481,974 B1
(45) Date of Patent: Jul. 9, 2013

(54) APPARATUS AND METHOD FOR MEASURING SINGLE CELL AND SUB-CELLULAR PHOTOSYNTHETIC EFFICIENCY

(75) Inventors: Ryan Wesley Davis, Pleasanton, CA (US); Seema Singh, Fremont, CA (US); Huawen Wu, Livermore, CA (US)

(73) Assignee: Sandia Corporation, Albuquerque, NM (US)

( * ) Notice: Subject to any disclaimer, the term of this patent is extended or adjusted under 35 U.S.C. 154(b) by 138 days.

(21) Appl. No.: 13/233,343

(22) Filed: Sep. 15, 2011

(51) Int. Cl.
*G01J 1/58* (2006.01)
*G01N 21/64* (2006.01)

(52) U.S. Cl.
CPC ............... *G01N 21/6428* (2013.01); *G01J 1/58* (2013.01)
USPC ...................................................... 250/459.1

(58) Field of Classification Search
CPC .................................................. G01N 21/6428
USPC ...................................................... 250/459.1
See application file for complete search history.

(56) References Cited

U.S. PATENT DOCUMENTS

| | | | |
|---|---|---|---|
| 6,573,512 B1 * | 6/2003 | Oberlin et al. ............. | 250/458.1 |
| 7,310,142 B2 | 12/2007 | Hayden et al. | |
| 7,435,876 B2 | 10/2008 | Jalink et al. | |
| 2005/0072935 A1 * | 4/2005 | Lussier ..................... | 250/458.1 |
| 2008/0219675 A1 | 9/2008 | Yano | |
| 2010/0111369 A1 * | 5/2010 | Lussier ..................... | 382/110 |
| 2010/0151443 A1 * | 6/2010 | Xiang et al. ..................... | 435/5 |

OTHER PUBLICATIONS

Beer, S.; Axelsson, L., "Limitations in the use of PAM fluorometry for measuring photosynthetic rates of macroalgae at high irradiances," European Journal of Phycology, 2004, v.39(1): pp. 1-7

Bischof, K.; Hanelt, D.; Aguilera, J.; Karsten, U.; Vögele, B.; Sawall, T.; Wiencke, C., "Seasonal variation in ecophysiological patterns in macroalgae from an Arctic fjord. I. Sensitivity of photosynthesis to ultraviolet radiation," Marine Biology, 2002, v.140: pp. 1097-1106.
Buschmann, C., "Photochemical and non-photochemical quenching coefficients of the chlorophyll fluorescence: comparison of variation and limits," Photosynthetica, 1999, v.37(2): pp. 217-224.
Cosgrove, J.; Borowitzka, M., "Applying Pulse Amplitude Modulation (PAM) fluorometry to microalgae suspensions: stirring potentially impacts fluorescence," Photosynthetic Research, 2006, v.88: pp. 343-350.

(Continued)

*Primary Examiner* — David Porta
*Assistant Examiner* — Edwin Gunberg
(74) *Attorney, Agent, or Firm* — Timothy P. Evans

(57) ABSTRACT

Devices for measuring single cell changes in photosynthetic efficiency in algal aquaculture are disclosed that include a combination of modulated LED trans-illumination of different intensities with synchronized through objective laser illumination and confocal detection. Synchronization and intensity modulation of a dual illumination scheme were provided using a custom microcontroller for a laser beam block and constant current LED driver. Therefore, single whole cell photosynthetic efficiency, and subcellular (diffraction limited) photosynthetic efficiency measurement modes are permitted. Wide field rapid light scanning actinic illumination is provided for both by an intensity modulated 470 nm LED. For the whole cell photosynthetic efficiency measurement, the same LED provides saturating pulses for generating photosynthetic induction curves. For the subcellular photosynthetic efficiency measurement, a switched through objective 488 nm laser provides saturating pulses for generating photosynthetic induction curves. A second near IR LED is employed to generate dark adapted states in the system under study.

5 Claims, 4 Drawing Sheets

OTHER PUBLICATIONS

Davis, R.W.; Carson, B.; Jones, H.D.T., Sinclair, M.B, "Hyperspectral Image Correlation for Monitoring Membrane Protein Dynamics in Living Cells" Proceedings of the SPIE, 2009, v.7184, Article No. 71840J, Three-Dimensional and Multidimensional Microscopy: Image Acquisition and Processing XVI, edited by Jose-Angel Conchello, J.-A.;Cogswell, C.J.; Wilson, T.

Juneau, P.; Harrison, P.J., "Comparison by PAM Fluorometry of Photosynthetic Activity of Nine Marine Phytoplankton Grown Under Identical Conditions," Photochemistry and Photobiology, 2005, v.81: pp. 649-653.

Minagawa, J., "Fluorescence quenching analysis," www.chlamy.org/companion/Fluorescence_Quenching.pdf, Doc. created Dec. 2, 2008.

Müller, P.; Li, X.-P.; Niyogi, K.K. "Non-Photochemical Quenching. A Response to Excess Light Energy," Plant Physiology, 2001, v.125: pp. 1558-1566.

Davis, R.W.; Aaron, J.S.; Rempe, S.L.; Timlin, J.A., "Fluorescence Fluctuation Analysis of Mixed Chromophores from a Line-Scanning Hyperspectral Imaging System," Proceedings of the SPIE, 2010 v.7570, Article No. 757002 "Three-Dimensional and Multidimensional Microscopy: Image Acquisition and Processing XVII," edited by Jose-Angel Conchello, J.-A.;Cogswell, C.J.; Wilson, T.; Brown, T.G.

Schreiber, U.; Bilger, W.; Neubauer, C., "Chlorophyll Fluorescence as a Nonintrusive Indicator for Rapid Assessment of In Vivo Photosynthesis," Ecophysiology of Photosynthesis (Schulze.E. E., Cladwell, M.M., Editors Springer-Verlag Publishers, 1994, pp. 49-70.

Sinclair, M.B.; Haaland, D.M.; Timlin, J.A.; Jones, H.D.T, "Hyperspectral confocal microscope," Applied Optics, 2006, v45(24): pp. 6283-6291.

Wu, H.; Volponi, J.V.; Oliver, A.E.; Parikh, A.N.; Simmons, B.A.; Singh, S., "In vivo lipidomics using single-cell Raman spectroscopy," 2011, Proceedings of the National Academy of Sciences of the United States of America, v108(9): pp. 3809-3814.

Van Kooten, O.; Snel, J.F.H.,"The use of chlorophyll fluorescence nomenclature in plant stress physiology," Photosynthesis Research, 1990, v25(3): pp. 147-150.

* cited by examiner

APPARATUS AND METHOD FOR MEASURING SINGLE CELL AND SUB-CELLULAR PHOTOSYNTHETIC EFFICIENCY

STATEMENT OF GOVERNMENT INTEREST

The United States Government has rights in this invention pursuant to Contract No. DE-AC04-94AL85000 between the United States Department of Energy and Sandia Corporation, for the operation of the Sandia National Laboratories.

CROSS-REFERENCE TO RELATED APPLICATIONS

This Application claims benefit of prior co-pending application 61/384,790 filed Sep. 21, 2010, and entitled "APPARATUS FOR MEASURING SINGLE CELL AND SUB-CELLULAR PHOTOSYNTHETIC EFFICIENCY," herein incorporated by reference.

BACKGROUND

Field of the Invention

The present invention relates generally to spectroscopic interrogation of cell structures of simple plants, particularly algae, and their response to environmental challenges. More particularly, the invention relates to the design of an optical spectrometer design and a custom microcontroller for performing rapid light scanning of single plant cells and sub-cellular structures in single plant cells, such as chloroplasts, using modified pulse amplitude modulated fluorescence spectrometry, and as a means for determining the local photosynthetic efficiencies of these structures.

Bulk photosynthetic efficiency measurements of microalgal suspensions suffer from artifacts and replication difficulties as a result of sample flocculation, cellular motility, and other inhomogeneities. A previous report has documented these effects concluding that one potential solution, sample stirring, introduces additional confounding artifacts (Cosgrove J., Borowitzka M., "Applying pulse amplitude modulated (PAM) fluorometry to microalgal suspensions: stirring potentially impacts fluorescence," *Photosynthesis Research*, 2006, v. 88: pp. 343-350). These problems can be effectively mediated, however, by employing a strategy which measures photosynthetic efficiency on single plant cells.

SUMMARY

The purpose of the invention, therefore, was to create a device capable of measuring the changes in photosynthetic efficiency, i.e., the fraction of light energy converted into chemical energy during photosynthesis in single cells of plant matter induced by changes in environmental factors related to growth and development. This was achieved by employing a combination of intensity modulated LED trans-illumination with synchronized through-objective laser illumination and confocal detection. Synchronization and intensity modulation of the dual illumination scheme were provided by using a custom designed microcontroller for a laser beam block and constant current LED driver. With this apparatus, two complementary measurement modes are permitted: 1) single, whole-cell photosynthetic efficiency; and 2) diffraction limited, sub-cellular photosynthetic efficiency. In both cases, wide field rapid light scanning using actinic illumination is provided by an intensity-modulated 470 nm LED. In the case of the whole-cell photosynthetic efficiency measurement, the same LED provides saturating pulses for generating photosynthetic induction curves. For the sub-cellular photosynthetic efficiency measurement, a switched through-objective 488 nm laser provides saturating pulses for generating photosynthetic induction curves. Finally, a second near-IR LED is employed to rapidly generate a dark adapted state in the plant systems under study.

BRIEF DESCRIPTION OF THE DRAWINGS

The accompanying drawings illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF ONE OR MORE EMBODIMENTS

Figure 1:
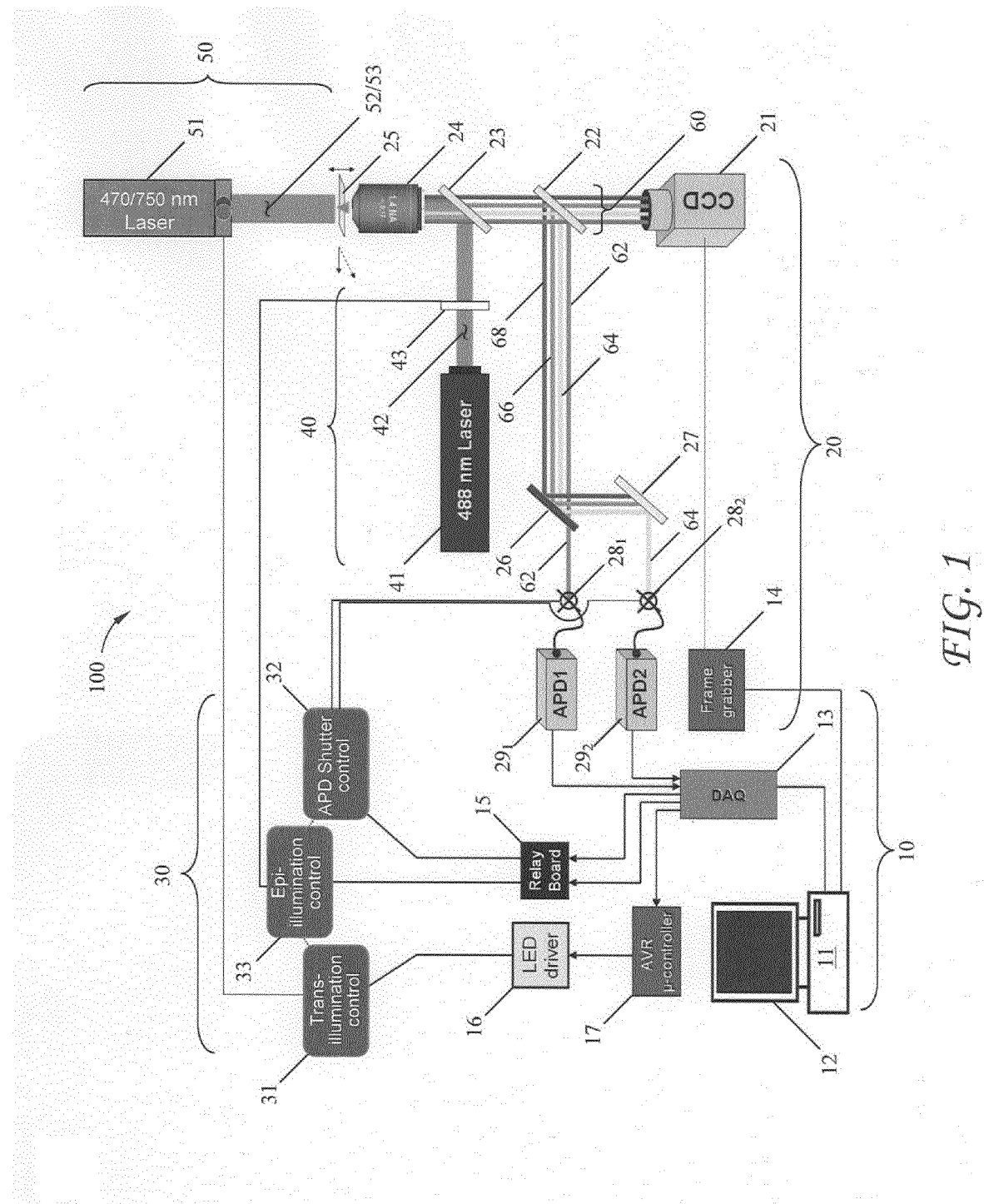
FIG. 1 shows a detailed schematic of one embodiment of the optical detection device.

The purpose of the invention was to create a device capable of measuring changes in single-cell photosynthetic efficiency induced by environmental factors in algal aquaculture. This was achieved with a dual illumination scheme employing a combination of intensity modulated LED trans-illumination, and synchronized, through-objective laser illumination and confocal detection. Synchronization and intensity modulation of the dual illumination scheme were provided using a custom micro-controller for a laser beam block and a constant current LED driver. Using this apparatus, two complimentary measurement modes were permitted: single, whole-cell photosynthetic efficiency, and sub-cellular (diffraction limited) photosynthetic efficiency. In both cases, wide field rapid light scanning actinic illumination is provided by an intensity-modulated 470 nm LED. In the case of the whole-cell photosynthetic efficiency measurement, the same LED provides saturating pulses for generating photosynthetic induction curves. In the case of the sub-cellular photosynthetic efficiency measurement, a switched, through-objective 488 nm laser provides saturating pulses for generating the photosynthetic induction curves. Finally, a second near-IR LED was employed to rapidly generate dark adapted states in the photosystem under study.

The dual illumination optical detection device 100, disclosed herein, comprises optics control modules 10 and 30; optical detection module 20; first and second light sources 40, 50; and translatable x-y microscope stage 25. Optics control module 10 further comprises a microprocessor 11, which itself comprises visual display 12, a data acquisition recorder 13, electrically communicating with an automatic voltage regulation (AVR) microcontroller 17, an LED driver 16 and a relay board 15.

Optics control module 30 comprises actinic trans-illumination source controller 31, avalanche photodiode (APD) shutter control 32 and epi-illumination (i.e., illumination and detection from one side of the sample) source control 33, each of which electrically interface with various components of optical module 10 such that each is under the control of microprocessor 11. In particular, data acquisition recorder 13 provides an electrical interface between APD shutter control 32 and with epi-illumination source control 33 and microprocessor 11. APD shutter control 32, in turn, electrically communicates with dichroic fiber optic couplings $28_1$ and $28_2$ which are themselves optically coupled, respectively, with APD $29_1$ and $29_2$ such that both couplings $28_1$ and $28_2$ act as binary gates to restrict light from entering either or both of APD $29_1$ and $29_2$ when APD shutter control 32 switches either or both of dichroic fiber optic couplings $28_1$ and $28_2$ "on" or "off" at the direction of microprocessor 11. APD $29_1$ and $29_2$ are themselves in electrical communication with DAQ 13 thereby providing a feed-back loop to microprocessor 11. Moreover, DAQ recorder 13 is also in electrical communication with AVR microcontroller 17 and LED driver 16 which are electrically coupled in series with actinic trans-illumination source controller 31 such that each can be controlled by microprocessor 11. Finally, optical module 10 further comprises frame grabber 14 in electrical communication with charge couple diode (CCD) camera 21. Frame grabber 14, therefore, acts as an interface with part of optical detection module 20 in order to provide for copying and storing images of the subject matter under observation.

Radiation for illuminating plant matter is supplied by epi-illumination source module 40 and by dual illumination source module 50. Source 40 comprises LED source 41 providing actinic radiation 42 at a wavelength of about 488 nm and epi-illumination shutter 43 electrically coupled with and driven by epi-illumination control 33. Dual source 50 comprises dual LED 51 providing infrared radiation 52 at a wavelength of greater than about 750 nm and actinic radiation 53 at a wavelength of about 470 nm.

Optical detection module 20 comprises CCD camera 21 for receiving light beam 60 output from microscope objective 24. Light beam 60 is itself comprised of the light response of plant matter illuminated by either or both of beams 42 and 53 generated by epi-illumination source module 40 and dual illumination source module 50. Light beam 60 therefore might be expected to comprise a plurality of light rays having wavelengths covering the full ranges of the visible spectrum corresponding to red 62, yellow 64, green 66, and blue 68 rays output from the sample being investigated (not shown), and collected by objective 24 and passed through blue long pass dichroic filter 23. Beam 60 is the split by beam splitter 22 which divides beam 60 equally between CCD camera 21 and short pass dichroic filter 26 which passes only red wavelengths 62 between about 670 nm to about 700 nm to first dichroic fiber optic coupling $28_1$ and reflects all other wavelengths onto long pass dichroic filter 27 which itself reflects only yellow wavelengths 64 between about 575 nm to about 585 nm into second dichroic fiber optic coupling $28_2$ while allowing all other wavelengths to pass through (not shown). Finally, depending upon the timing sequence generated by microprocessor 11, the first and second dichroic fiber couples $28_1$ and $28_2$ may be enabled allowing light to enter either or both of APD $29_1$ and $29_2$, thereby providing an electronic signal proportional to the intensity of the light signal received by APD $29_1$ and/or $29_2$.

In operation, device 100 functions as follows. A quantity of plant matter, such as algae, is exposed to known environmental conditions while growing. Cells obtained from a quantity of plant matter of interest are placed on a transparent substrate (not shown), mounted onto translatable microscope stage 25, and the stage moved to center the cell sample under microscope objective 24. Once microscope stage 25 is properly positioned, microprocessor 11 commands trans-illumination source controller 31 to drive LED dual source 51 to illuminate the plant cells from behind, exposing them to a flux of infrared (IR) radiation 52, having a wavelength of greater than about 750 nm. This pre-conditioning is done because exposure to IR radiation is known to "drain" off native charge in the plant cells in excited states, thereby returning the these cells to a ground state.

Once the plant cells have been pre-conditioned by infrared radiation microscope 52, microprocessor 11 now commands trans-illumination source controller 31 to again illuminate the cells from behind with actinic radiation 53 from dual LED source 51 at a wavelength of about 470 nm. This initial illumination stimulates the endogenous chromophores in the plant cells to fluoresce and provide the baseline light signal $F_0$ shown in FIG. 2. The plant cells are then exposed to a short saturating light pulse from above (epi-illumination), again driven by microprocessor 11, directing epi-illumination control 33 to open shutter 43 such that LED source 41 supplies actinic radiation 42 at a wavelength of 488 nm through microscope objective 24, while the background trans-illumination light actinic radiation 53 remains "on." The epi-illumination pulse is focused on specific areas of an individual cell in order to stimulate that area within the cell. This results in a sharp spike in detected fluorescence which rapidly decays, subsequently, to a steady state value Light will excite chlorophyll a of photo-system (PS) II into its excited state where it can then transfer an electron into the electron transport chain (ETC) between PS II and PS I. As electrons are transferred through the ETC, the initial electron acceptor in PS II is depleted ("opens") and is able to accept a new electron. Under high light conditions, this system will eventually become saturated, as all reaction centers will become occupied by electrons. When the reaction centers are occupied ("closed"), new electrons cannot be accepted at the rate at which chlorophyll a is being excited, and the chlorophyll will release the excess energy in the form of fluorescence light.

The efficiency with which light energy is utilized by a plant cell is a function of the health of that cell. When plant cells are under stress, their photo-systems can become saturated more easily. As such, these systems do not process light as efficiently as un-stressed cells. By interrogating plant cells as described below, it is possible to measure how effectively these cells convert light energy into chemical energy, i.e., to measure the photosynthetic efficiency of the cell.

Figure 2:
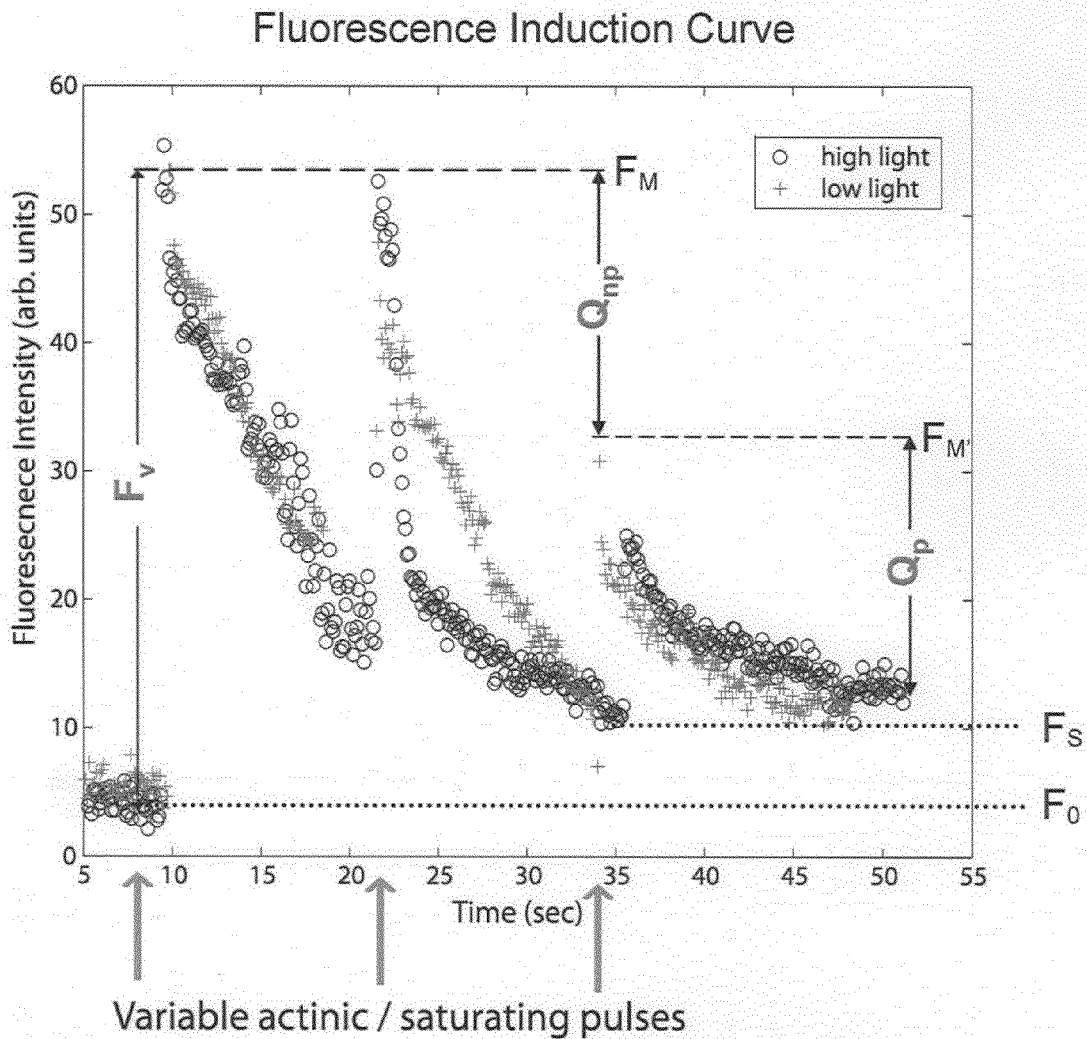
FIG. 2 shows a fluorescence induction curve used to measure the photosynthetic efficiency of an unknown sample of plant matter.

In order to measure the photosynthetic efficiency of an unknown sample of plant matter, that sample is first dark-adapted (or treated with far red IR radiation as described above) for a period of time so that all of electron acceptors in the reaction centers are "open" and able to accept electrons. The fluorescence of this system is measured when the most light energy can be accepted into the ETC for photochemistry by initially illuminating the sample with a continuous source of actinic light. The measured fluorescence of this initial response is designated as $F_0$, as shown in FIG. 2. The sample is then exposed to a high intensity pulse of actinic light modulated on the continuous background light in order to saturate all of the electron acceptors and thereby close the reaction centers. All absorbed light energy at this point will then be given off as a pulse of fluorescent light, $F_M$. As shown in FIG. 2, the difference between the initial fluorescence, $F_0$, and the maximum measured fluorescence, $F_M$, is defined as the variable fluorescence, $F_V$. It is known that $F_V$ normalized to $F_M$, i.e., $F_V/F_M$, is taken to be a measure of the maximum photosynthetic efficiency of dark-adapted plant cells.

Figure 3:
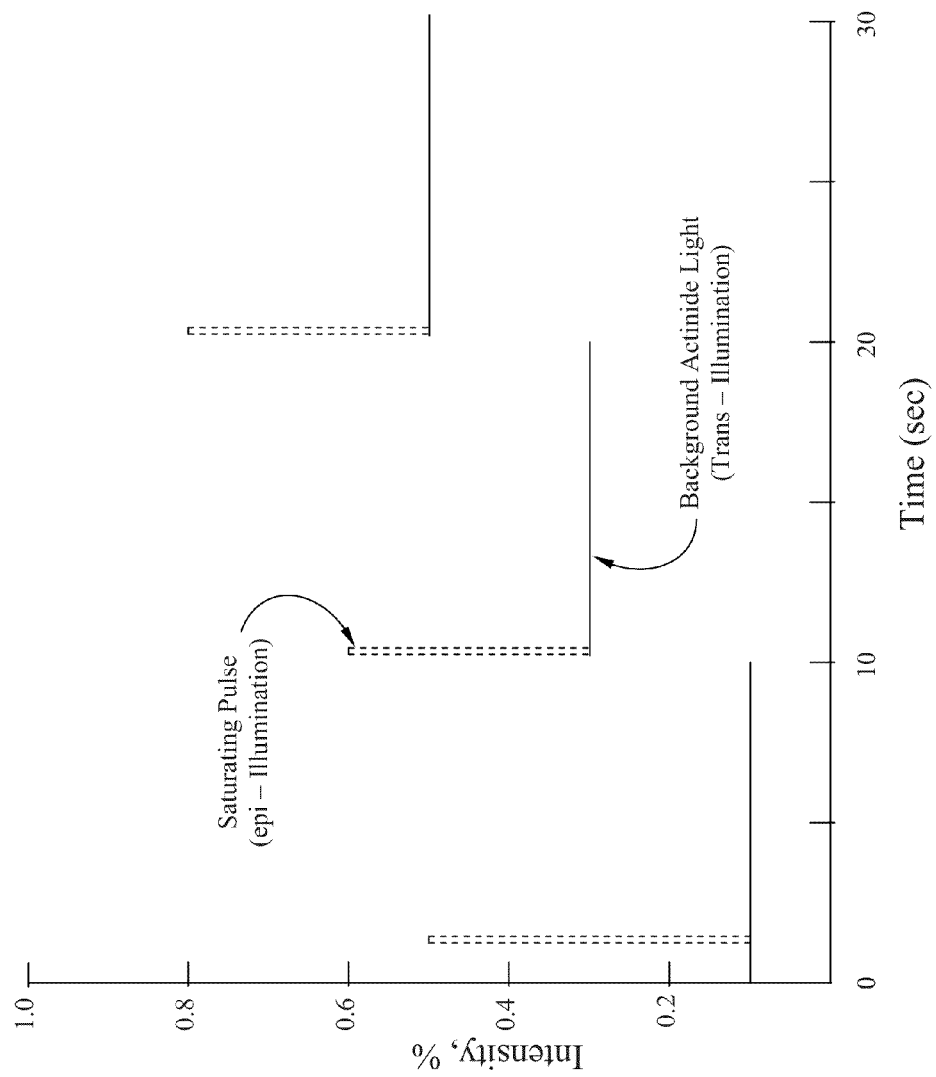
FIG. 3 shows a measurement technique for determining photosynthetic efficiency during light adaption, wherein the intensity of photosynthetically active radiation intensity is stepped up after an initial saturating pulse such that subsequent saturating pulses are interleaved onto a background actinic light source in order to scan the photosynthetically active radiation intensity range of an identified sample.

To obtain a measure of the photosynthetic efficiency during light adaption, an additional light induction curve measurement is made. During this measurement, following the initial saturating pulse, the intensity of photosynthetically active radiation intensity is stepped up, as shown in FIG. 3, and subsequent saturating pulses are interleaved on the background actinic light source to scan the photosynthetically active radiation intensity range of the sample.

Upon continuous illumination with moderately excess light, a combination of mechanisms, known as photochemical quenching ($Q_P$, the decrease in fluorescence yield due to excitation energy being used for photochemical reactions, i.e., photosynthesis) and non-photochemical quenching ($Q_{NP}$, several protective non-photochemical mechanisms developed by plants and used during photosynthesis to dissipate excess energy as heat), lowers the fluorescence yield generated by the saturating pulses. Again, as shown in FIG. 2, $Q_{NP}$ can be seen as the difference between $F_M$ and the measured maximum fluorescence after a later saturating light pulse, $F_{M'}$, during illumination. Moreover, $Q_P$ is found to be the difference between the maximum measure fluorescence of the later saturating light pulse and the background steady state light level, $F_S$.

Figure 4:
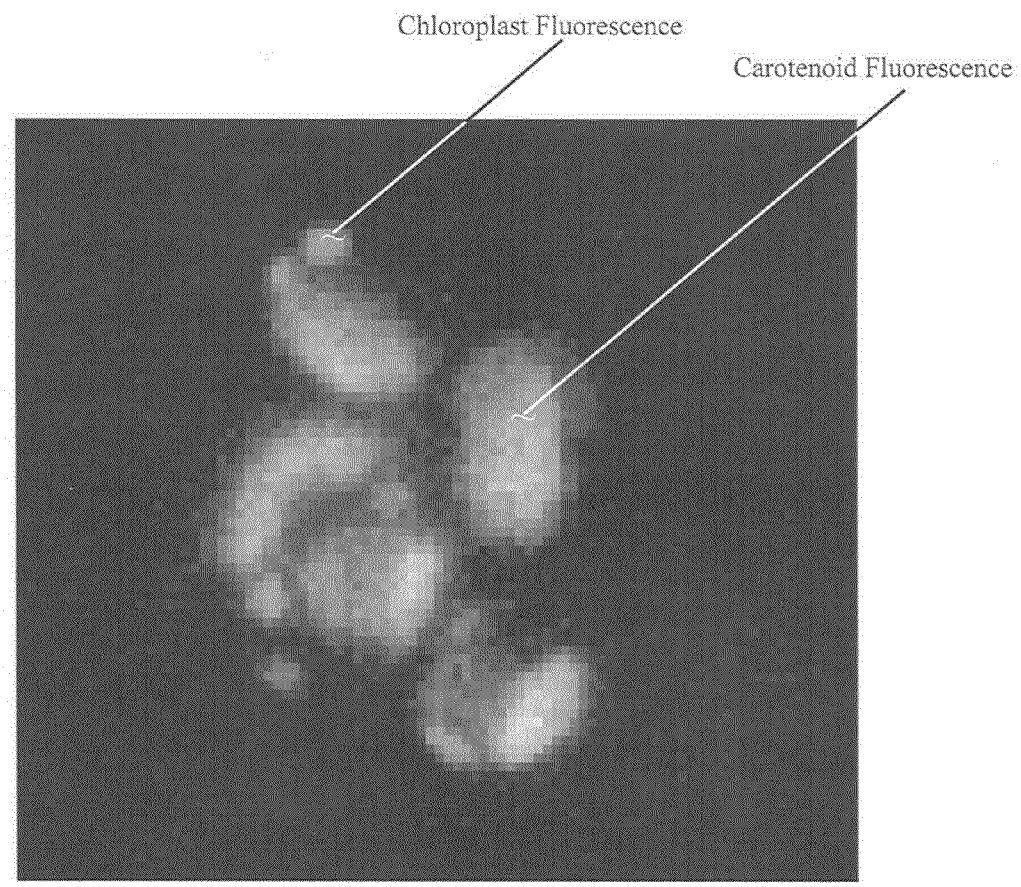
FIG. 4 shows an example of a pixilated image of several plant cells having various regions, therein showing differing levels/colors of fluorescence.

FIG. 4 shows an example of a pixilated image of several plant cells having various regions therein, showing differing levels/colors of fluorescence.

From the foregoing, it will be appreciated that, although specific embodiments of the invention have been described herein for purposes of illustration, various modifications and other alternatives, or adaptations may be made without deviating from the spirit and scope of the invention. Accordingly, the present invention is not limited to the specific embodiments as illustrated herein, but is only limited by the following claims.

Finally, to the extent necessary to understand or complete the disclosure of the present invention, all publications, patents, and patent applications mentioned herein are expressly incorporated by reference therein to the same extent, as though each were individually so incorporated.

What is claimed is:

1. An optical detection system, comprising:
   an optics control module, comprising, a microprocessor in electrical communication with a data acquisition (DAQ) recorder and with a charged coupled diode (CCD) camera, the DAQ recorder in electrical communication with first and second illumination source controls and an avalanche photodiodes (APD) shutter control in electrical communication with first and second dichroic fiber optic couplings, the DAQ recorder in further electrical communication with first and second APD optically communicating with the first and second dichroic fiber optic couplings;
   an optical detection module comprising an objective lens, a first long pass dichroic filter receiving light passed by the objective lens, a beam splitter, and the CCD camera, the beam splitter dividing the light passing through the first long pass dichroic filter between the CCD camera and a short pass dichroic filter passing only red wavelengths of light to the first dichroic fiber optic coupling, the short pass filter re-directing all remaining wavelengths of the light re-directed by the beam splitter into a second long pass filter configured to re-direct only yellow wavelengths of light into the second dichroic fiber optic coupling, wherein the first and second dichroic fiber optic couplings optically communicate with the first and second APD, respectively;
   a first LED light source comprising a source of actinic radiation having a wavelength of about 488 nm and a light source shutter in electrical communication with the first illumination source control, wherein control and operation of the light source shutter is performed by the microprocessor;
   a second LED light source comprising a source of actinic radiation having a wavelength of about 470 nm and a source of infrared radiation having a wavelength of greater than about 750 nm, the second light source in electrical communication with the second illumination source control wherein control and operation of the second LED light source is performed by the microprocessor; and
   a translatable x-y microscope stage, wherein the translatable microscope stage positions a sample of plant matter under the objective lens.

2. The optical detection system of claim 1, further comprising a relay board, wherein the relay board provides an electrical interface between the DAQ recorder, the first illumination source control and the APD shutter control.

3. The optical detection system of claim 1, further comprising an automatic voltage regulation (AVR) microcontroller electrically communicating with an LED driver, wherein the microcontroller/LED driver combination provides an electrical interface between the DAQ recorder and the second illumination source control.

4. The optical detection system of claim 1, wherein the an optics control module further comprises a frame grabber in electrical communication between the microprocessor and the CCD camera.

5. A method for determining the light-adapted photosynthetic efficiency of one or more individual cells within a macroscopic region of plant matter, comprising the steps of:
   a) irradiating a first macroscopic region of plant matter with a beam of infrared electromagnetic radiation comprising wavelengths greater than 750 nm;
   b) irradiating the first macroscopic region with a beam of actinic electromagnetic radiation comprising wavelengths of about 480 nm-490 nm and having a first background intensity;
   c) irradiating one or more individual cells within the first macroscopic region of plant matter with a first high intensity, focused pulse of actinic electromagnetic radiation comprising wavelengths at or near 470 nm;
   d) measuring and recording an intensity of a first fluorescence response in the one or more individual cells as the intensity of the first fluorescence response decays over time from a first maximum intensity to a baseline fluorescence intensity;
   e) calculating a first photosynthetic efficiency equal to the first maximum fluorescence intensity minus the baseline fluorescence intensity;
   f) again irradiating the first macroscopic region of plant material with a beam of actinic electromagnetic radiation comprising wavelengths of about 480 nm-490 nm having a second background intensity greater than the first background intensity;
   g) again irradiating the one or more individual cells within the first macroscopic region of plant matter with a second high intensity focused pulse of actinic electromagnetic radiation comprising wavelengths at or near 470 nm, h) measuring and recording an intensity of a second fluorescence response in the one or more individual cells as the intensity of the second fluorescence response decays over time from a second maximum intensity to a baseline fluorescence intensity;

i) calculating a second photosynthetic efficiency equal to the second maximum fluorescence intensity minus the baseline fluorescence intensity; and j) calculating a second photosynthetic efficiency equal to the second maximum fluorescence intensity minus the baseline fluorescence intensity, wherein the second photosynthetic efficiency is equal to the light-adapted photosynthetic efficiency of the plant material.

* * * * *